United States Patent
Ishihara et al.

(10) Patent No.: US 12,246,033 B2
(45) Date of Patent: *Mar. 11, 2025

(54) CONSTITUENT FOR PREVENTING AND/OR TREATING SKIN WOUNDS

(71) Applicants: NATIONAL INSTITUTE FOR MATERIALS SCIENCE, Tsukuba (JP); SUMITOMO SEIKA CHEMICALS CO., LTD., Hyogo (JP); UNIVERSITY OF THE RYUKYUS, Okinawa (JP)

(72) Inventors: Shinsuke Ishihara, Tsukuba (JP); Nobuo Iyi, Tsukuba (JP); Shigeki Sakaue, Hyogo (JP); Manabu Kakinohana, Okinawa (JP)

(73) Assignees: NATIONAL INSTITUTE FOR MATERIALS SCIENCE, Tsukuba (JP); SUMITOMO SEIKA CHEMICALS CO., LTD., Hyogo (JP); UNIVERSITY OF THE RYUKYUS, Okinawa (JP)

( * ) Notice: Subject to any disclaimer, the term of this patent is extended or adjusted under 35 U.S.C. 154(b) by 507 days.

This patent is subject to a terminal disclaimer.

(21) Appl. No.: 17/620,571

(22) PCT Filed: Jun. 15, 2020

(86) PCT No.: PCT/JP2020/023341
§ 371 (c)(1),
(2) Date: Dec. 17, 2021

(87) PCT Pub. No.: WO2020/262054
PCT Pub. Date: Dec. 30, 2020

(65) Prior Publication Data
US 2022/0354885 A1    Nov. 10, 2022

(30) Foreign Application Priority Data

Jun. 28, 2019   (JP) .................................. 2019-122422

(51) Int. Cl.
A61K 33/04    (2006.01)
A61P 17/02    (2006.01)

(52) U.S. Cl.
CPC .............. *A61K 33/04* (2013.01); *A61P 17/02* (2018.01)

(58) Field of Classification Search
None
See application file for complete search history.

(56) References Cited

U.S. PATENT DOCUMENTS 4,572,174 A * 2/1986 Eilender ................ A61G 7/057
128/889
2007/0078113 A1   4/2007 Roth et al.
2009/0041859 A1   2/2009 Mizutani et al.
2013/0052289 A1 * 2/2013 Chiang .................... A61P 17/02
424/769
2013/0253051 A1   9/2013 Xian et al.
2015/0045711 A1 * 2/2015 Taylor ..................... A61L 15/58
604/338
2015/0336050 A1   11/2015 Kanatzidis et al.
2017/0304334 A1   10/2017 Takata et al.
2018/0271789 A1 * 9/2018 Sung ........................ A61P 17/02
2019/0038643 A1   2/2019 Wang
2019/0046681 A1   2/2019 Squire et al.
2019/0298756 A1   10/2019 Prinz et al.
2021/0269231 A1   9/2021 Ishihara et al.
2022/0233579 A1   7/2022 Prinz et al.

FOREIGN PATENT DOCUMENTS

| | | |
|---|---|---|
| CN | 107987105 A | 5/2018 |
| CN | 109793919 A | 5/2019 |
| JP | 2001-212170 A | 8/2001 |
| JP | 2005-335965 A | 12/2005 |
| JP | 2008-538569 A | 10/2008 |
| JP | 2009-191015 A | 8/2009 |
| JP | 2010-077143 A | 4/2010 |
| JP | 2011-219411 A | 11/2011 |
| JP | 2015-120646 A | 7/2015 |
| JP | 2015-193000 A | 11/2015 |
| JP | 2016-077514 A | 5/2016 |
| JP | 2019-507622 A | 3/2019 |
| WO | 2012/075242 A2 | 6/2012 |
| WO | 2018/083326 A1 | 5/2018 |
| WO | 2020/012994 A1 | 1/2020 |

OTHER PUBLICATIONS

PCT/ISA/210, "International Search Report for International Application No. PCT/JP2020/023341," Aug. 25, 2020.
Lin, W.C,. et al., "In situ depot comprising phase-change materials that can sustainably release a gasotransmitter H2S to treat diabetic wounds", Biomaterials, 2017, vol. 145, pp. 1-8, in particular, fig. 1.
Wu, J. et al., "Novel H2S releasing nanofibrous coating for in vivo dermal wound regeneration", ACS Appl. Mater. Interfaces, 2016, vol. 8, p. 27474-27481 in particular, fig. 2, 4.
China National Intellectual Property Administration, "Office Action with Search Report for Chinese Patent Application 202080047327.8," Oct. 18, 2022.

(Continued)

*Primary Examiner* — Melissa S Mercier
*Assistant Examiner* — Caralynne E Helm
(74) *Attorney, Agent, or Firm* — HAUPTMAN HAM, LLP

(57) ABSTRACT

The invention provides a constituent that is used with a novel method for preventing and/or treating skin wounds and ensures stable delivery of low-concentration hydrogen sulfide to a wound site. The skin wound-preventing and/or treating constituent includes a sustained hydrogen sulfide releasing agent that is preferably a layered double hydroxide having HS— and/or Sk2− between layers where k is a positive integer.

7 Claims, 8 Drawing Sheets

(56) References Cited

OTHER PUBLICATIONS

European Patent Office, "Extended European Search Report with Search Opinion for European Patent Application 20832769.2," Jun. 23, 2023.

Rives Vicente et al, "Intercalation of drugs in layered double hydroxides and their controlled release: A review", Applied Clay Science, Elsevier, Amsterdam, NL, vol. 88, Dec. 28, 2013, pp. 239-269, XP028826819, ISSN 0169-1317, DOI:10.1016/J.CLAY. 2013.12.002.

Mohamed A. Othman et al, "Selectivity of layered double hydroxides and their derivative mixed metal oxides as sorbents of hydrogen sulfide", Journal of Hazardous Materials, vol. 254-255, Jun. 1, 2013, pp. 221-227, XP055084063, ISSN 0304-3894, DOI:10.1016/j. jhazmat.2013.03.030.

* cited by examiner

FIG. 7(a)  FIG. 7(b)
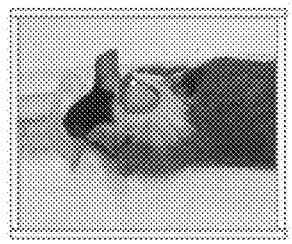 Sustained Loading 12 hours 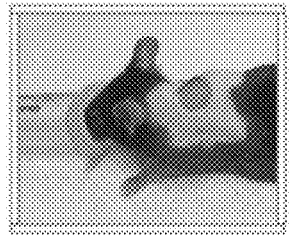
FIG. 8
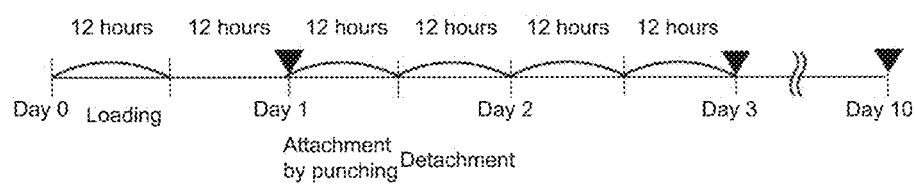
FIG. 9(a)  FIG. 9(b)  FIG. 9(c)
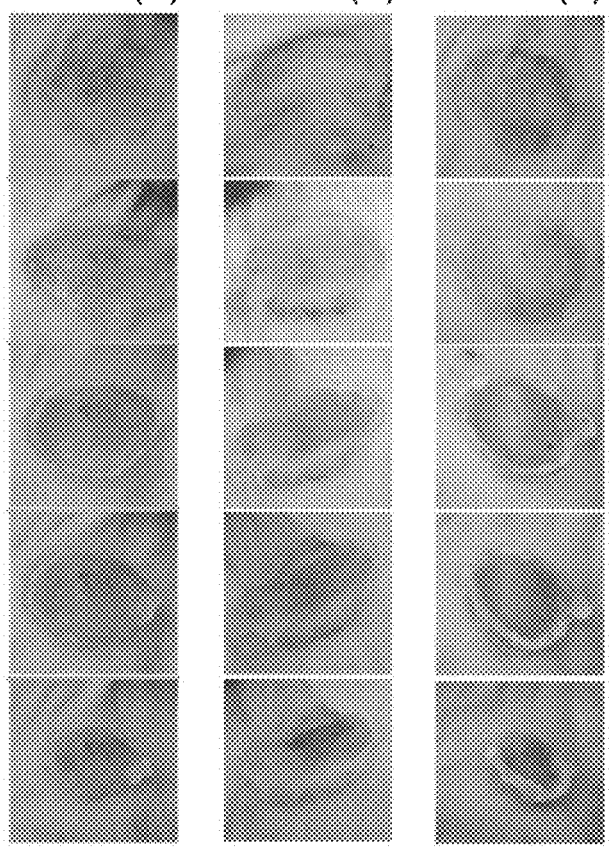
Day1
Day3
Day6
Day8
Day10

CONSTITUENT FOR PREVENTING AND/OR TREATING SKIN WOUNDS

RELATED APPLICATIONS

The present application is National Phase of International Application No. PCT/JP2020/023341 filed Jun. 15, 2020, and claims priority from Japanese Application No. 2019-122422, filed Jun. 28, 2019, the disclosure of which is hereby incorporated by reference herein in its entirety.

BACKGROUND ART

Being physical damage to surface tissues of the body, the wound is a general term for wounds with or without openings.

In most cases, a slight wound heals over naturally without recourse to any particular treatment. A severe wound usually heals over by way of natural healing power, too, if it is properly treated by suturing, skin grafting, etc.

There are, however, not a few cases where wound healing takes too long time with respect to intractable ulcers such as bedsores, venous stasis ulcers, arterial ulcers, diabetic ulcers and radiation ulcers. In some cases, it takes too long time for patients undergoing an operation to heal operative wound primarily because of a lowering of their natural healing power caused by their own diseases or medication.

Of such intractable wounds, the bedsore observed in long bedridden patients is a necrotic skin ulcer caused by a long-standing application of certain or higher pressures to the skin.

In recent years, accompanied by the progression of aging population, patients suffering from bedsores while spending long confined to bed have tended to increase in number. To deal with this situation, various proposals of therapeutic drugs or methods for treating wounds inclusive of bedsores.

For instance, Patent Publication 1 discloses that sodium glutamate is orally administrated to patients in the form of an internal medicine, and Patent Publication 2 discloses that a wound treating agent containing glutamine, polydexstrose, lactulose and befidobacteria is orally administrated to patients.

Referring to an external preparation and its administration method, Patent Publication 3 discloses that an external preparation containing either one of hydrophilic or white petrolatum and povidone iodine is coated on a wound surface. Also, Patent Publication 4 discloses that hydrogen-containing water is used as a liquid for external use in which a bedsore site is immersed, the hydrogen-containing water is added dropwise onto the bedsore site and a coating means soaked with the hydrogen-containing water is affixed to the bedsore site. Further, Patent Publication 5 discloses that cotton gauze soaked with fradiomycin sulfate and trafermin is packed in the back of an ulcer. Furthermore, Patent Publication 6 discloses that a "wound coating material" composed of a sponge layer containing crosslinked hyaluronic acid, silver sulfadiazine and crosslinked alginic acid and an unwoven fabric layer is applied to a wound surface.

On the other hand, hydrogen sulfide ($H_2S$)-containing spa has been used for folk remedies from old, because it has been known to be efficacious against skin diseases or circulatory diseases. However, hydrogen sulfide ($H_2S$) is difficult to handle on a daily basis because of its toxicity. In recent years, this hydrogen sulfide has been reported to have bioactivities such as cell protective action, blood vessel relaxing action, antioxidant action, neurotransmission regulation action and apoptosis inhibition action under low concentration conditions.

As such biological activities of hydrogen sulfide have been clearly understood, brisk trials of applying this to medical treatments are now under way.

For instance, Patent Publication 7 discloses that viability of mice is improved when they are exposed to a $H_2S$ atmosphere at 80 ppm to place them in "stasis conditions" where their activity is recovered.

Patent Publication 8 discloses a technical idea wherein a fluid having a therapeutic gas having vasodilatory action such as hydrogen sulfide is added or exposed to a biocompatible polymer matrix containing a polymer and closed cells and comprising a surface configured to come in direct contact with a wound site to store said therapeutic gas in said polymer matrix thereby delivering said therapeutic gas to said wound site.

PRIOR ARTS

Patent Publications

Patent Publication 1: JP(A) 2009-191015
Patent Publication 2: JP(A) 2015-120646
Patent Publication 3: JP(A) 2010-77143
Patent Publication 4: JP(A) 2011-219411
Patent Publication 5: JP(A) 2016-77514
Patent Publication 6: JP(A) 2001-212170
Patent Publication 7: Japanese Unexamined Patent Application Publication No. 2008-538569
Patent Publication 8: Japanese Unexamined Patent Application Publication No. 2019-507622

SUMMARY OF THE INVENTION

Problems to be Solved by the Invention

As described above, various methods have so far been reported to treat wounds inclusive of bedsores, and various medical treatment methods harnessing the bioactivity of hydrogen sulfide are reported too.

However, there is no report so far about whether or not hydrogen sulfide delivered to a wound site is actually efficacious. The technical idea set forth in Patent Publication 8 has a doubt about the capability of delivering a low-concentration therapeutic gas in a stable manner because the therapeutic gas is stored in an amount greater than 10000 ppm (1%) inside the closed cells in the biocompatible polymer matrix (FIG. 11, etc.). Referring to hydrogen sulfide in particular, the stable delivery of it in low concentrations is important because it is harmful to many species of life in high concentrations.

Accordingly, the present invention has for its object to provide a constituent applicable to a novel method for preventing and/or treating skin wounds by delivering low-concentration hydrogen sulfide to a wound site.

EMBODIMENT OF THE INVENTION

As a result of various studies made for the purpose of achieving the aforesaid object, the present inventors have accomplished the present invention by finding that a constituent comprising a sustained hydrogen sulfide releasing agent is applied to a skin wound thereby enhancing an effect on the healing of said wound site.

In other words, one embodiment of the invention configured to achieve the aforesaid object provides a constituent for preventing and/or treating skin wounds is characterized by containing a sustained hydrogen sulfide releasing agent.

Advantages of the Invention

According to the invention disclosed herein, it is possible to provide a constituent for ensuring stable delivery of low-concentration hydrogen sulfide so that it can be applied to a novel method for preventing and/or treating skin wounds.

BRIEF EXPLANATION OF THE DRAWINGS

FIGS. 7(a) and 7(b) are illustrative of bedsore formation employed in Example 1 and Comparative Examples 1 and 2, respectively.

FIG. 8 is illustrative of how a skin wound is treated by the constituents for preventing and/or treating skin wounds used in Example 1 and Comparative Examples 1 and 2, respectively, and of a bedsore area measurement protocol.

FIGS. 9(a), 9(b) and 9(c) are sets of photographs showing bedsore states in Example 1 and Comparative Examples 1 and 2 ((a): Comp. Ex. 1, (b): Comp. Ex. 2, (c): Ex. 1).

MODES FOR CARRYING OUT THE INVENTION

By way of example but not by way of limitation, the present invention is now explained in greater details with reference to one embodiment thereof.

Figure 1:
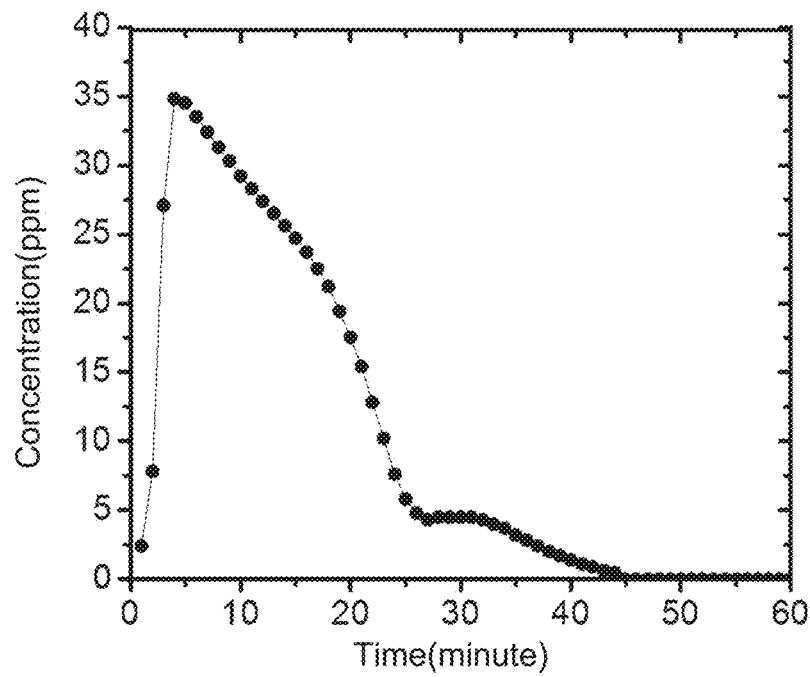
FIG. 1 is an exemplary graph illustrative of the results of $H_2S$ release experimentation with a sustained hydrogen sulfide releasing agent used in one embodiment of the invention.

The constituent for preventing and/or treating skin wounds (hereinafter called the "constituent according to the present embodiment") according to one embodiment of the invention (hereinafter called the "present embodiment") contains a sustained hydrogen sulfide releasing agent. It is here noted that the "constituent for preventing and/or treating skin wounds" refers to a constituent that is applied directly to the skin so that a skin wound can be prevented and/or treated. It is also noted that the "sustained hydrogen sulfide releasing agent" refers to a substance capable of allowing hydrogen sulfide having a concentration of at least $1/100$ of the maximum value to be continuously detected over 30 minutes or longer in the following $H_2S$ release experimentation. In the result of $H_2S$ release experimentation shown in FIG. 1 as an example, the maximum value of detected $H_2S$ concentration is about 35 ppm; if $H_2S$ having a concentration of 0.35 ppm that is $1/100$ of that value or greater is continuously detected over 30 minutes or longer, it is judged as providing a sustained hydrogen sulfide releasing agent.

It is here noted that the aforesaid "capable of allowing hydrogen sulfide having a concentration of at least $1/100$ of the maximum value to be continuously detected over 30 minutes or longer in the $H_2S$ release experimentation" is also called the "sustained hydrogen sulfide releasability". In this case, improvements or enhancements in the sustained hydrogen sulfide releasability are understood to mean that in the aforesaid $H_2S$ release experimentation, there is a lower maximum value obtained in the same or longer detection time or, alternatively, there is hydrogen sulfide detected over a longer time of period with the same or smaller maximum value.

The aforesaid $H_2S$ release experimentation is carried out by the following process.

A gas inlet tube and a gas outlet tube are inserted through a closed vessel loaded with the material to be measured, air of 20° C. and 50% RH is introduced through the gas inlet tube into the vessel at a flow rate of 100 mL/minute, and the concentration of $H_2S$ in air coming out of the gas outlet tube is measured every 1 minute to observe changes over time in the $H_2S$ concentration. It is here noted that the measurement interval may be adjusted between 1 minute and 5 minutes depending on sustained release time.

Although the $H_2S$ concentration sensor used for concentration measurement is ToxiRAE 3 (with a detection limit of 0.4 ppm and a resolution of 0.1 ppm) made by RAE Systems Inc., other equivalents may be used too. In place of the $H_2S$ concentration sensor, a detector tube, gas chromatography or other concentration measuring method may also be used. For instance, when the detector tube (produced by Gastec Corporation) is used, the discharge gas collected within a prescribed period of time of 1 to 5 minutes with a Tedlar (registered trademark) bag or the like is measured by a detector tube method.

The aforesaid sustained hydrogen sulfide releasing agent is preferably a layered double hydroxide having $HS^-$ and/or $S_k^{2-}$ (where k is a positive integer) that provides a hydrogen sulfide source inserted between layers (hereinafter called the "sulfide ion-containing LDH).

Figure 2:
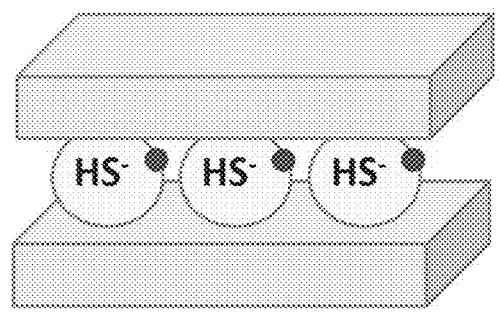
FIG. 2 is a conceptual view indicative of the structure of a sulfide ion-containing LDH.

As schematically shown in FIG. 2, the sulfide ion-containing LDH has a structure having $HS^-$ and/or $S_k^{2-}$ (where k is a positive integer) inserted between the layers of a layered double hydroxide (LDH). Note here that $HS^-$ is a hydrogen sulfide ion, and $S_k^{2-}$ is a sulfide ion where k=1, and a polysulfide ion where k≥2. The sulfur-containing anion positioned between LDH layers is considered to be mainly $HS^-$ reflecting the existing ratios of the ion species in the aqueous solution used for production; however, it would be difficult to specify the ion species because there are various ion species and oxidized state coexisting. The "$HS^-$ and/or $S_k^{2-}$ (where k is a positive integer)" is herein used as a wording that comprehensively encompasses sulfur-containing anions that provide a hydrogen sulfide source. For simplification, $HS^-$ alone is indicated in the drawing; but actually it is considered that the ion species described above besides $HS^-$ are intermingled.

Unlike many other inorganic layered compounds, LDH is a few compounds capable of having anions between layers because each layer is positively charged. For this reason, it is considered that LDH can intercalate $HS^-$ and/or $S_k^{2-}$ among the layers.

The sulfide ion-containing LDH is preferably represented by the following general formula (1):

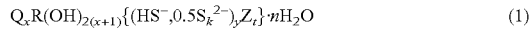

$$Q_xR(OH)_{2(x+1)}\{(HS^-,0.5S_k^{2-})_yZ_t\}\cdot nH_2O \quad (1)$$

where Q is a divalent metal ion, R is a trivalent metal ion, and Z is an anion other than $HS^-$ or $S_k^{2-}$. In formula (1), x is a number that satisfies 1.8≤x≤4.2, y is a number that satisfies 0.01≤y≤2.0, t is a number that satisfies 0≤t≤1.0, and n is a number that changes or varies depending on an environmental humidity.

In formula (1), Z is an anion derived from the starting material or solvent used for production of the sulfide ion-containing LDH, or an atmosphere prevailing during production or storage of the sulfide ion-containing LDH, as exemplified by $OH^-$, $Cl^-$, $Br^-$, $I^-$, $F^-$, $NO_3^-$, $ClO_4^-$, $SO_4^{2-}$, $CO_3^{2-}$, an acetate anion ($CH_3COO^-$), a propionate anion ($CH_3CH_2COO^-$), a lactate anion ($CH_3—CH(OH)—COO^-$), and an isethionate anion ($HOC_2H_4SO_3^-$).

It is here noted that as mentioned above, sulfur in the anions positioned between the LDH layers is present in various oxidized states, rendering it difficult to specify ion species. Therefore, for expressing the sulfide ion-containing LDH in terms of general formulae, the sulfur-containing anions that provide a hydrogen sulfide source are represented by "$HS^-$, $0.5S_k^{2-}$".

Referring to the sulfide ion-containing LDH represented by the aforesaid general formula (1), it is more preferable that the aforesaid Q is selected from the group consisting of $Mg^{2+}$, $Mn^{2+}$, $Fe^{2+}$, $Co^{2+}$, $Ni^{2+}$, $Cu^{2+}$, $Zn^{2+}$ and $Ca^{2+}$ and the aforesaid R is selected from the group consisting of $Al^{3+}$, $Ga^{3+}$, $Cr^{3+}$, $Mn^{3+}$, $Fe^{3+}$, $Co^{3+}$ and $Ni^{3+}$. Most preferably, the aforesaid Q is $Mg^{2+}$ and the aforesaid R is $Al^{3+}$.

An MgAl type layered double hydroxide containing Mg and Al, which is the most common solid material among layered double hydroxides, is now produced in an industrial scale because of being capable of synthesis at low costs (for instance, synthesized Hydrotalcite made by Kyowa Chemical Industry Co., Ltd.). This material does not give rise to any problem at all even upon adherence to the skin or the like, and is used with gastrointestinal drugs (antacids) or the like. Further, it has been studied as a drug delivery system (DDS) carrier from a medical standpoint, and applied to medical fields with some achievements. For this reason, the sulfide ion-containing LDH having an MgAl type layered double hydroxide as a fundamental structure wherein the aforesaid Q is $Mg^{2+}$ and the aforesaid R is $Al^{3+}$ could be improved in terms of safety.

A preferable aspect of the present embodiment using the sulfide ion-containing LDH as a sustained hydrogen sulfide releasing agent is based on the finding that the sulfide ion-containing LDH sustainably releases off hydrogen sulfide by contact with the air, as set forth in Japanese Patent Application No. 2018-132081. Sustained hydrogen sulfide release mechanism by the sulfide ion-containing LDH is considered as being due to the fact that a conjugate base intercalated between LDH layers is protonated by $H_2CO_3$ resulting from contact of atmospheric $CO_2$ with $H_2O$ to form the corresponding weak acid molecule that is released off in the atmosphere when it is of volatility. When the sulfide ion-containing LDH comes in contact with the air, these anions will be released off as $H_2S$ in the air, because $HS^-$ and $S_k^{2-}$ are conjugate bases of weak acid $H_2S$.

The chemical reaction in this case is expressed by the following chemical formula (2):

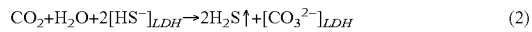

$$CO_2+H_2O+2[HS^-]_{LDH} \rightarrow 2H_2S\uparrow+[CO_3^{2-}]_{LDH} \quad (2)$$

(where $[\ ]_{LDH}$ shows that the anions in the brackets are present between the LDH layers).

Figure 3:
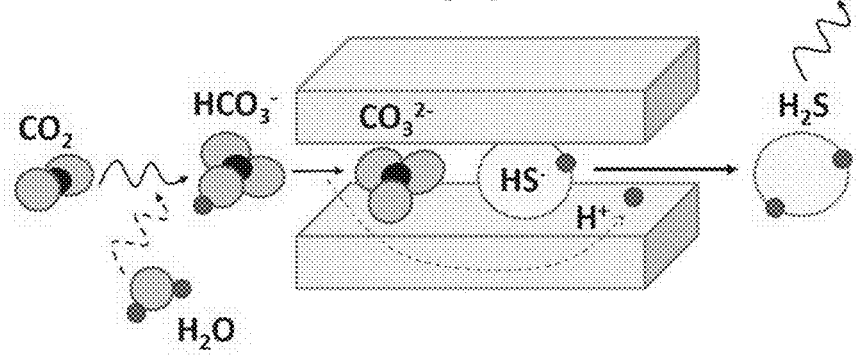
FIG. 3 is a schematic view indicating the mechanism through which hydrogen sulfide is released out of the sulfide ion-containing LDH.

As shown in FIG. 3, this series of reactions would be considered as taking place through a process wherein the atmospheric $CO_2$ enters between the layers of the sulfide ion-containing LDH, reacting with the atmospheric or interlayer $H_2O$ to form protons $H^+$ and $CO_3^{2-}$ ions, and the ensuing $CO_3^{2-}$ anion exchanges with interlayer $HS^-$ and/or $S_k^{2-}$ simultaneously with the ensuing combining with $HS^-$ and/or $S_k^{2-}$ to form hydrogen sulfide ($H_2S$) that is then released off in the atmosphere. This essentially requires a diffusion process comprising entrance of gas between layers and detachment of gas from between the layers, and consequently it is considered that the aforesaid reactions is continued over an extended period of time, which is observed as sustained release of hydrogen sulfide.

Figure 4:
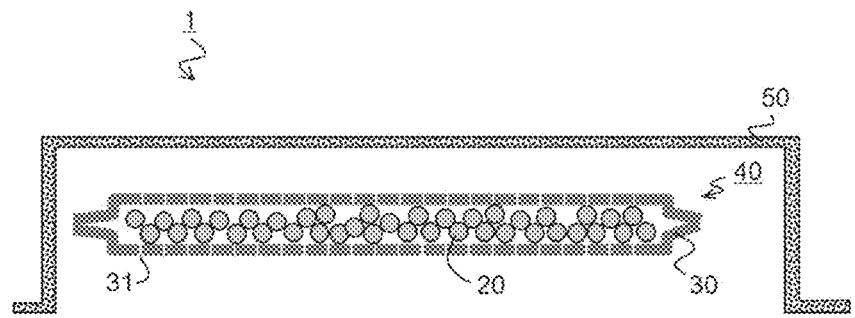
FIG. 4 is a conceptual view indicating one example of the structure of a constituent for preventing and/or treating skin wounds according to one embodiment of the invention.

The constituent according to the present embodiment may be used in any desired shape, structure and state as long as it contains the aforesaid sustained hydrogen sulfide releasing agent as a constituent component. Referring to FIG. 4 as an example, a sustained hydrogen sulfide releaser 40 formed by encapsulating a sustained hydrogen sulfide releasing agent 20 within a breathable cover or sheet 30 is covered with a dressing material 50.

Figure 5A:
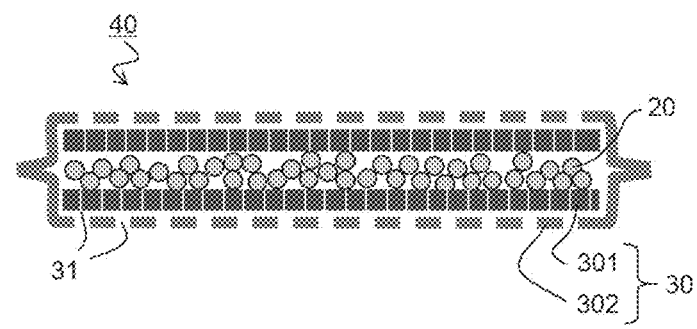
FIGS. 5(a) and 5(b) are conceptual views showing one embodiment of the structure of a cover or sheet usable with the constituent for preventing and/or treating skin wounds as exemplarily shown in FIG. 4.
Figure 5B:
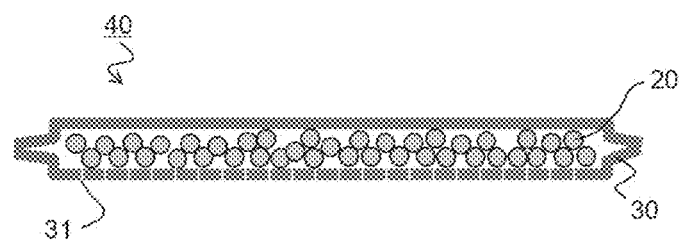

In this case, the cover or sheet 30 may have a function of delivering hydrogen sulfide released out of the sustained hydrogen sulfide releasing agent 20 to any desired site by any desired amount. The cover or sheet 30 used herein is preferably of such flexibility as to be deformed conforming with the shape of an application site; a porous tape or sheet such as a commercially available surgical tape is preferably used. The cover or sheet 30 is preferably in a porous form having a multiplicity of fine through-holes 31, 31, thereby adjusting the delivery amount of hydrogen sulfide by a relatively simple means such as selection and regulation of pores in terms of diameter and number. In view of regulation of delivery amounts and delivery sites of hydrogen sulfide, as shown in FIG. 5(a), a plurality of covers or sheets 301, 302, each having breathability, are stacked up to regulate the delivery amount of hydrogen sulfide or, alternatively, one surface may be composed of a breathable material while another surface may be composed of an non-breathable material, as shown in FIG. 5(b), allowing hydrogen sulfide to be released out of one surface alone.

The sustained hydrogen sulfide releasing agent 20 loaded or encapsulated in the breathable cover or sheet 30 may be in a granulated or compacted powder state obtained through powder densification treatment, whereby the surface area of the sustained hydrogen sulfide releasing agent 20 decreases per mass; hence, the released hydrogen sulfide is hardly to be dispersed in an environment, resulting in enhanced sustained hydrogen sulfide releasability. In addition, when the sulfide ion-containing LDH is used as the sustained hydrogen sulfide releasing agent, the generation of hydrogen sulfide is prevented due to prevention of contact with carbon dioxide and moisture that may otherwise contribute to hydrogen sulfide release, resulting in much improved sustained hydrogen sulfide releasability.

The densification process includes, but is not limited to, a granulation process such as rolling granulation or spray-dry granulation, a press molding process such as a uniaxial press molding process, or a process for consolidation upon put in the cover or sheet 30.

It is here noted that in view of enhancing sustained hydrogen sulfide releasability due to a decrease in the surface area of the sustained hydrogen sulfide releasing agent 20 per mass, it is also useful to simply increase the thickness of the sustained hydrogen sulfide releasing agent loaded and piled up in the cover or sheet 30.

The sustained hydrogen sulfide releasing agent may be mixed with an extender and then loaded in the breathable cover or sheet 30, thereby decreasing the amount of the sustained hydrogen sulfide releasing agent and, at the same time, reducing the amount of released hydrogen sulfide to enhance sustained hydrogen sulfide releasability. In addition, when the sulfide ion-containing LDH is used as the sustained hydrogen sulfide releasing agent, contact with carbon dioxide and moisture, which may otherwise contribute to hydrogen sulfide release, is also restrained by the extender so that the sustained hydrogen sulfide releasability can be much more improved.

There is no particular limitation on the extender usable herein provided that it does neither release nor react with hydrogen sulfide; examples are an inorganic materials inclusive of silica, alumina, layered double hydroxides and glass, and an organic materials such as fats and oils, and resins.

The sustained hydrogen sulfide releaser 40 formed by encapsulating the sustained hydrogen sulfide releasing agent 20 in the cover or sheet 30 is covered with the dressing material 50 into a constituent 1 according to the present embodiment, as shown in FIG. 4. Use of the dressing material 50 ensures that any leakage of hydrogen sulfide released out of the sustained hydrogen sulfide releaser 40 into an environment is held back, leading to accelerated wound healing and decreased nasty odors. Further, any misalignment of the sustained hydrogen sulfide 40 can be avoided, too. Furthermore, it is possible to form a wetting environment around a wound via the primary action of the dressing material. For this purpose, an ordinary dressing material may be used, such as Air Wall (registered trademark), Cathereep (registered trademark), Tegaderm (registered trademark), and Surgit (registered trademark).

When the present constituent 1 containing the aforesaid sustained hydrogen sulfide releaser 40 is used for treatment of a skin wound, it may further comprise a pad that comes into contact with said wound to absorb an effusion. For this purpose, an ordinarily used medical pad may be employed, inclusive of, in addition to general medical gauze, Derma Aid (registered trademark) and Plus moist (registered trademark).

Figure 6:
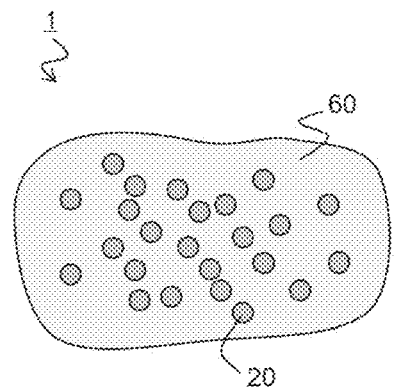
FIG. 6 is a conceptual view showing another example of the structure of a constituent for preventing and/or treating skin wounds according to one embodiment of the invention.

Referring to another example of the constituent according to the present embodiment, examples include ointment and so on in which the powdery sustained hydrogen sulfide releasing agent 20 is mixed with and dispersed in a substrate 60, as depicted in FIG. 6. This constituent is easy to apply and regulate in terms of application range and amount because it is applied by coating to the skin.

Referring to the substrate used herein, examples include a substrate usually used with ointment or the like, typically hydrocarbons such as white petrolatum and liquid paraffin, waxes such as beeswax and lanoline, fatty acid esters such as isopropyl myristate, fatty acids such as stearic acid and oleic acid, and alcohols such as stearyl alcohol and cetanol as well as jelly, gels and creams.

As the aforesaid constituent is applied to the skin, it could cause hydrogen sulfide released out of the sustained hydrogen sulfide releasing agent 20 in a fixed concentration to be delivered to the skin stably over an extended period of time, contributing more to prevention of wounds and/or treatment of wounds.

When the constitute according to the present embodiment is used for treatment of wounds, the concentration of hydrogen sulfide delivered to a wound site is preferably 0.1 ppm to 40 ppm, and more preferably 0.5 ppm to 20 ppm with a view to improving healing effects. Alternatively, the hydrogen sulfide concentration may be in a range of 0.0005 ppm to 1000 ppm, 0.001 ppm to 800 ppm, 0.0025 ppm to 600 ppm, 0.005 ppm to 400 ppm, 0.0075 ppm to 200 ppm, 0.01 ppm to 100 ppm, 0.025 ppm to 90 ppm, 0.05 ppm to 80 ppm, and 0.075 ppm to 60 ppm. This concentration of hydrogen sulfide may be regulated depending on the type of sustained hydrogen sulfide releasing agent used (including compositions having formula (1) in the case of using the sulfide ion-containing LDH), its amount, the diameter and number of through-holes 31, 31, . . . in the breathable cover or sheet 30, the layer construction of the breathable cover or sheet 30 and so on.

It is here noted that the hydrogen sulfide concentration herein is based on volume.

The concentration of hydrogen sulfide delivered from the constituent according to the present embodiment to a wound site may be estimated by any one of the following procedures.

The constituent according to the present embodiment is placed on the detector of an $H_2S$ concentration senor to measure the $H_2S$ concentration per minute, thereby checking up $H_2S$ concentration changes over time. It is here noted that the measurement interval may be adjusted between 1 minute and 5 minutes depending sustained release time. As occasion demands, the constituent according to the present embodiment and/or the detector of the $H_2S$ concentration sensor may further be covered with a dressing material or the like to check up $H_2S$ concentration changes over time within closed space by the aforesaid procedure. Although the $H_2S$ concentration sensor used for concentration measurement is ToxiRAE 3 made by RAE Systems Inc. (with detection limit of 0.4 ppm and a resolution of 0.1 ppm), any other equivalent may be used, too.

A detector tube may be used in place of the $H_2S$ concentration sensor. The detector tube used herein may be either a short-term detector tube of the type of inhaling a sample gas at a certain flow rate or a long-term detector tube of the type of determining an average gas concentration for a certain time by natural diffusion alone without recourse to sample gas inhalation (passive Dosi-tube). Referring to the measurement of concentrations within closed space, when the inside volume of closed space is small and there is no sample gas inhaled by the short-term detector tube, the long-term detector tube (passive Dosi-tube) is advantageously used. A variety of detector tubes made by Gastec Corporation may be used for this purpose. In one example of measurement by the long-term detector tube, the constituent according to the present embodiment is put on the skin of the living organism to be treated, and the skin is then covered with a dressing material or the like to form closed space with the dressing material and the skin in which the long-term detector tube is inserted to measure the concentration of $H_2S$.

A minute quantity of sample gas may be collected by a micro-syringe and then subjected to concentration measurement by gas chromatography or other methods.

Another embodiment associated with the invention in terms of technical idea (hereafter called the "associated embodiment") encompasses a method for preventing skin wounds wherein the sustained hydrogen sulfide releasing agent-containing constituent is applied to the skin of the living organism, and a method for treating skin wounds wherein said constituent is applied to a wound in the skin of the living organism. In what follows, this associated embodiment will be explained in details.

In the associated embodiment, the constituent according to the aforesaid embodiment is applied to the skin of a living organism such that hydrogen sulfide sustainably released out of the sustained hydrogen sulfide releaser is diffused to a wound site.

Referring to one exemplary application method, if the aforesaid constituent includes the sustained hydrogen sulfide releaser and dressing material, said dressing material may then be affixed or stuck to the skin. When a wound is then treated by the application of said constituent, said constituent is affixed in place such that the wound is covered with said dressing material.

Referring to another exemplary application method, if the aforesaid constituent is ointment or the like comprising a powdery sustained hydrogen sulfide releasing agent mixed with and dispersed into a substrate, it may be coated onto the skin. When said constituent is applied for treatment of wound, it may be coated onto the wound.

Although there is no particular limitation on the concentration of hydrogen sulfide delivered from the constituent of the present embodiment to a wound site, it is preferably 0.1 ppm to 40 ppm, and more preferably 0.5 ppm to 20 ppm with a view to enhancing healing effects. Alternatively, the hydrogen sulfide concentration may be in a range of 0.0005 ppm to 1000 ppm, 0.001 ppm to 800 ppm, 0.0025 ppm to 600 ppm, 0.005 ppm to 400 ppm, 0.0075 ppm to 200 ppm, 0.01 ppm to 100 ppm, 0.025 ppm to 90 ppm, 0.05 ppm to 80 ppm, and 0.075 ppm to 60 ppm. This concentration of hydrogen sulfide may be regulated depending on the type of sustained hydrogen sulfide releasing agent used (including compositions having formula (1) in the case of using the sulfide ion-containing LDH), its amount, the diameter and number of through-holes in the breathable cover or sheet, the layer construction of the breathable cover or sheet and so on.

EXAMPLES

The present invention will now be specifically explained on the basis of examples; however, these examples are given as an aid for an easy understanding of the present invention, but not by way of limitation.

Example 1

In Example 1 and Comparative Examples 1 and 2, an exemplary constituent for treating skin wounds, comprising a sustained hydrogen sulfide releaser and a dressing material, was used to make a study of the efficacy of the invention against a bedsore model.

<Preparation of the Sustained Hydrogen Sulfide Releaser>

A sustained hydrogen sulfide releaser including a sulfide ion-containing LDH was prepared as the sustained hydrogen sulfide releasing agent according to the following procedures.

LDH(MgAl-LDH2) expressed by general formula $Mg_2Al(OH)_6(CO_3^{2-})_{0.5}\cdot 2H_2O$ with Mg ions as the divalent metal ions and Al ions as the trivalent metal ions was synthesized and used as the carbonate type LDH. Hereafter, this LDH will be referred to as $CO_3^{2-}$MgAl-LDH2.

First of all, $CO_3^{2-}$MgAl-LDH2 was synthesized according to the process set forth in JP(A) 2005-335965.

$MgCl_2 \cdot 6H_2O$ (508 mg) and $AlCl_3 \cdot 6H_2O$ (302 mg) were weighed and added with ion-exchange water to prepare a 12.5 mL solution to and with which a 12.5 mL aqueous solution having hexamethylenetetramine (613 mg) dissolved therein was added and mixed. Then, the ensuing solution was filtrated through a 0.2 μm membrane filter, and then loaded in a pressure-resistant Teflon(registered trademark) container having a capacity of 50 mL, which was then placed and tightly sealed in a pressure-resistant stainless steel container for hydrothermal treatment at 140° C. for 1 day. After hydrothermal treatment, the mixture was filtrated, washed with water, and dried in vacuo to obtain 279 mg of white powders.

The obtained white powders had a particle diameter of about 0.5 to 2 μm and an Mg/Al molar ratio of 1.94 (±0.04) with FTIR (Fourier transform infrared absorption) spectra conforming to the already reported profile.

Then, the resultant carbonate type LDH ($CO_3^{2-}$MgAl-LDH2) was converted to the Cl type LDH. 80.7 mg of $CO_3^{2-}$ MgAl-LDH2 were weighed and placed in a three-neck flask, and added with 43.3 mL of ethanol to prepare a suspension. 6.7 mL of an ethanol solution of hydrochloric acid (0.1 mol/L) were added dropwise to the suspension while stirred by a magnetic stirrer for a 1-hour reaction at 35° C. under a nitrogen flow (500 mL/min) with stirring. Thereafter, filtration was carried out in a nitrogen flow using a membrane filter having a pore diameter of 0.2 μm, and the precipitates were fully washed with ethanol. After filtration, the precipitates were raked up and collected, immediately followed by decompression and drying under vacuum for 1 hour or longer to obtain white powders.

As a result of measurement of FTIR (Fourier transform infrared absorption) of the obtained white powders, there was no adsorption of 1360 $cm^{-1}$ by carbonate ions ($CO_3^{2-}$) observed. From this, it has been judged that the carbonate ions are substituted by chloride ions. From the result of analysis by ICP-AES (SPS1700HVR made by Seiko), it has been found that there is no Mg/Al molar ratio change. In what follows, this LDH will be referred to as Cl⁻MgAl-LDH2.

40.5 mg of Cl⁻MgAl-LDH2 were placed in a 50 mL glass vial. On the other hand, 36.6 mg of NaHS·nH$_2$O were dissolved in 30 mL of ion-exchange water, which had been already degassed by boiling under nitrogen gas bubbling, to prepare an NaHS solution. The aforesaid NaHS solution was added to the aforesaid glass vial for ultrasonic dispersion, after which the glass vial was tightly sealed up for a two-day reaction at room temperature. The total amount of the post-reaction liquid was filtrated through a membrane filter (a hydrophilic PTFE membrane filter of 0.2 μm and operations of washing filtrates (residues) with 2 mL of degassed ion-exchange water were repeated five times. Another membrane filter of the same type was placed on the membrane filter having filtrates (residues) deposited thereon such that the residues were put between two membrane filters. Thereafter, portions of the membranes on which the residues were deposited were hollowed out in circular form together with the membrane filters by a leather punch of 6 mm in diameter, then placed on an adhesive surface of a porous tape (Keep-Pore(registered trademark) made by Nichiban Co., Ltd.), and then bonded and sandwiched by another porous tape from above. This was dried under a vacuum for about 2 hours to obtain a sustained hydrogen sulfide releaser.

The resultant sustained hydrogen sulfide releaser was tightly encapsulated in an aluminum laminated bag (Lamizip (registered trademark) AL-D made by Seisan Nihonsha LTD.) into a package. This package was tightly sealed in another aluminum laminated bag along with a deoxidizer (Ageless (registered trademark) made by Mitsubishi Gas Chemical Company, Inc.) and a tablet type desiccating agent (DO1056 made by Yamani Yakuhin Co., Ltd.). The processing operations described so far were all carried out in a glove box in which a nitrogen atmosphere prevailed.

The package was stored at normal temperature under the air until the time of using the sustained hydrogen sulfide releaser contained inside.

<Provision of the Living Organism to be Treated>

A mouse (C57BL/6 mouse at 8 weeks old) was anesthetized by isoflurane, and its back skin was put and pressed between two strong magnets as shown in FIG. 7(a) and held for 12 hours to form a bedsore as depicted in FIG. 7(b).

<Preparation of the Constituent for Treating Skin Wounds, Treatment Therewith, and Observation of Bedsores>

After removal of the load applied by strong magnets, a bedsore was treated with the constituent comprising the sustained hydrogen sulfide releaser for treating a skin wound and observed according to the protocol shown in FIG. 8. Specifically, 12 hours after load removal, the aforesaid package was opened in the air to take out the sustained hydrogen sulfide releaser and put it on the bedsore. Then, a dressing material (Airwall (registered trademark) made by skinix) was affixed in such a way to cover said sustained hydrogen sulfide releaser and the bedsore thereby forming and applying the constituent for treating skin wounds. After an elapse of 12 hours, said constituent for treating skin wounds was detached off and after an elapse of a further 12 hours, another constituent for treating skin wounds was created and applied according to similar procedures again. Subsequently, a cycle comprising application of the constituent for treating skin wounds for 12 hours and exposure to the air for 12 hours was repeated from the start of pressing by strong magnets until the elapse of ten days, and one day, 3 days, 6 days, 8 days and 10 days after the start of pressing, photographs were taken of the bedsore under anesthesia by isoflurane, and submitted to a third person dermatologist to get him or her to use Image J (Fuji) to measure the number of pixels with a ruler width of 1 cm. Then, with 10 units as one unit, the bedsore site was surrounded and this unit was used for area calculation to make a morphological estimation of healing process with the first day as 100%. It is here noted that as a result of measurement of hydrogen sulfide concentrations by use of a long-term detector tube (No. 4D made by Gastec Corporation) with another mouse (C57BL/6 mouse at 8 weeks old), a time load average concentration over 4 hours was 50 (ppm·hour).

Figure 10:
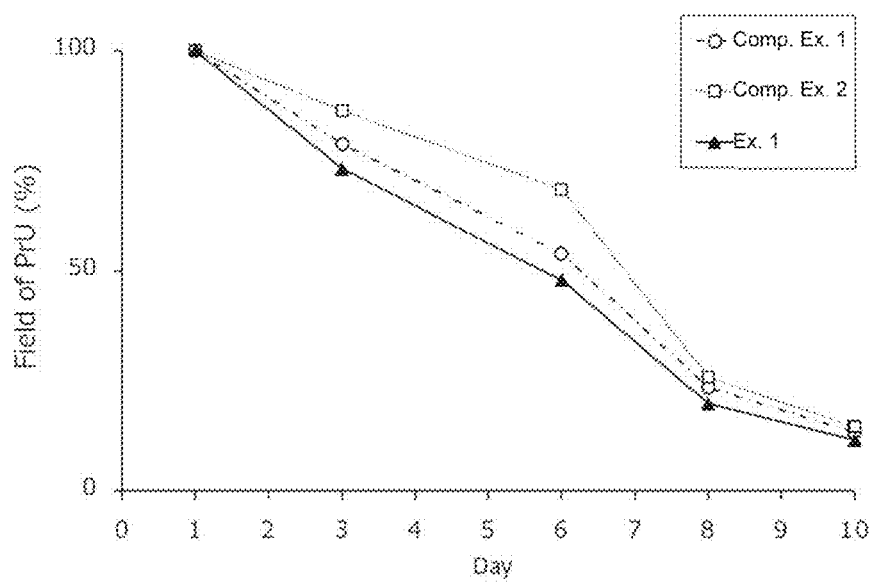
FIG. 10 is a graphical diagram indicative of the results of measurement of bedsore areas in Examples 1 as well as Comparative Example 1 and 2.

Photographs taken of the bedsore are attached hereto as FIG. 9(c), and the results of bedsore area measurement are shown by black triangular markers and a solid line in FIG. 10. Note here that the "Field of PrU (Pressure Ulcer) stands for a bedsore area.

Comparative Example 1

The treatment according to Comparative Example 1 was carried out as in Example 1 except that the sustained hydrogen sulfide releaser was not used in the preparation process of the constituent for treating skin wounds.

Photographs taken of the bedsore are attached hereto as FIG. 9(a), and the results of bedsore area measurement are shown by white circular markers and a dashed line in FIG. 10, respectively.

Comparative Example 2

Example 1 was repeated for treatment according to Example 1 except that no constituent for treating skin wounds was used.

Photographs taken of the bedsore are attached hereto as FIG. 9(b), and the results of bedsore area measurement are indicated by white square markers and a dotted line in FIG. 10, respectively.

From comparisons of FIG. 9(c) with FIGS. 9(a) and 9(b), it has been observed that there is an improvement in the bedsore state in the initial stage of treatment, and a considerable improvement is found from the start of pressing by strong magnets up to the sixth day.

From FIG. 10, it has also been found that the bedsore area in Ex. 1 is slightly smaller than that in Comp. Ex. 1 and considerably smaller than that in Comp. Ex. 2.

These results would show that there is a bedsore-healing effect obtained by application of the sustained hydrogen sulfide releasing agent-containing constituent for treating skin wounds.

Example 2

In Example 2 as well as Example 3 and Comparative Example 3 to be given later, a constituent comprising the inventive sustained hydrogen sulfide releaser and a dressing material for treating skin wounds were used to consider the effect of the invention on a skin excision model.

<Provision of the Living Organism to be Treated>

One day after a mouse (C57BL/6 mouse at 8-weeks old) was preoperatively shaven off at its back, t was anesthetized by isoflurane to hollow out the back skin through the cuticle and the derma using a biopsy trepan (made by Kai Industries, Co., Ltd.) having a diameter of 6 mm.

<Preparation of the Constituent for Treating Skin Wounds, Treatment Therewith, and Observation of a Skin Excision>

Figure 11:
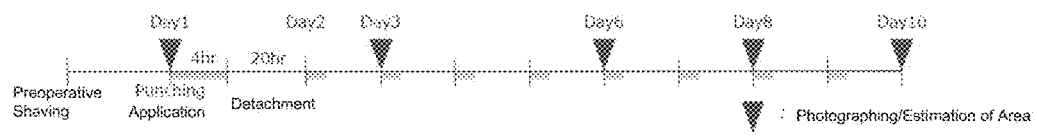
FIG. 11 is illustrative of how a skin wound is treated by the constituents for treating skin wounds used in Examples 2 and 3 as well as Comparative Example 3, respectively, and of a skin excision area measurement protocol.

The aforesaid mouse was treated with the constituent for treating skin wounds prepared as in Example 1 to observe a skin excision according to the protocol shown in FIG. 11. Specifically, immediately after the back skin was hollowed out, the aforesaid package was opened in the air to take out the aforesaid sustained hydrogen sulfide releaser and apply it to the skin excision. Then, a dressing material (Airwall (registered trademark) made by skinix) was affixed in such a way to cover said sustained hydrogen sulfide releaser and the skin excision thereby forming and applying the constituent for treating skin wounds. After an elapse of 4 hours, said constituent for treating skin wounds was detached off and after an elapse of a further 20 hours, the aforesaid constituent for treating skin wounds was formed and applied to the skin excision again. Subsequently, a cycle comprising 4-hour application of the constituent for treating skin wounds and 20-hours exposure to the air was repeated 9 times in total from the start of skin hollowing. Just after skin excision (Day 1 that stands for the number of days elapsed from preoperative shaving as will hereafter be applied), after the completion of two cycles (Day 3), after the completion of 5 cycles (Day 6), after the completion of 7 cycles (Day 8) and after the completion of 9 cycles (Day 10), photographs were taken of the skin excision under anesthesia by isoflurane, and submitted to a third person dermatologist to get him or her to make a morphological estimation of healing process. The photographs taken of the skin excision are attached hereto as FIG. 12(a), and the results of skin excision area measurement are indicated by a black triangular marker and a black solid line in FIG. 13, respectively. Note here that the "Wound Area" in FIG. 13 stands for the area of the skin excision.

Example 3

The treatment according to Example 3 was carried out as in Example 2 except that the occupied area of the sustained hydrogen sulfide releaser was reduced down to 4/9 in Example 2 (44.4%). Specifically, although the membrane filter containing sulfide ion-containing LDH was circularly hollowed out by a leather punch of 6 mm in diameter in Example 2, the membrane filter containing sulfide ion-containing LDH was circularly hollowed out by a leather punch of 4 mm in diameter in Example 3 to form the sustained hydrogen sulfide releaser.

Figures 12A, 12B, 12C:
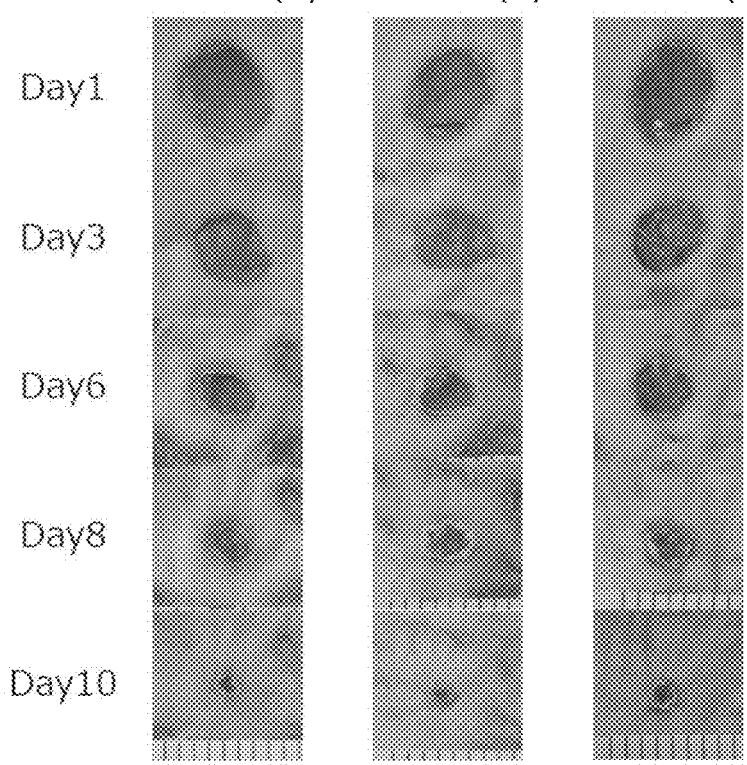
FIGS. 12(a), 12(b) and 12(c) are sets of photographs showing states of skin excisions in Examples 2 and 3 as well as Comparative Example 3 ((a): Ex. 2, (b): Ex. 3, (c): Comp. Ex. 3).
Figure 13:
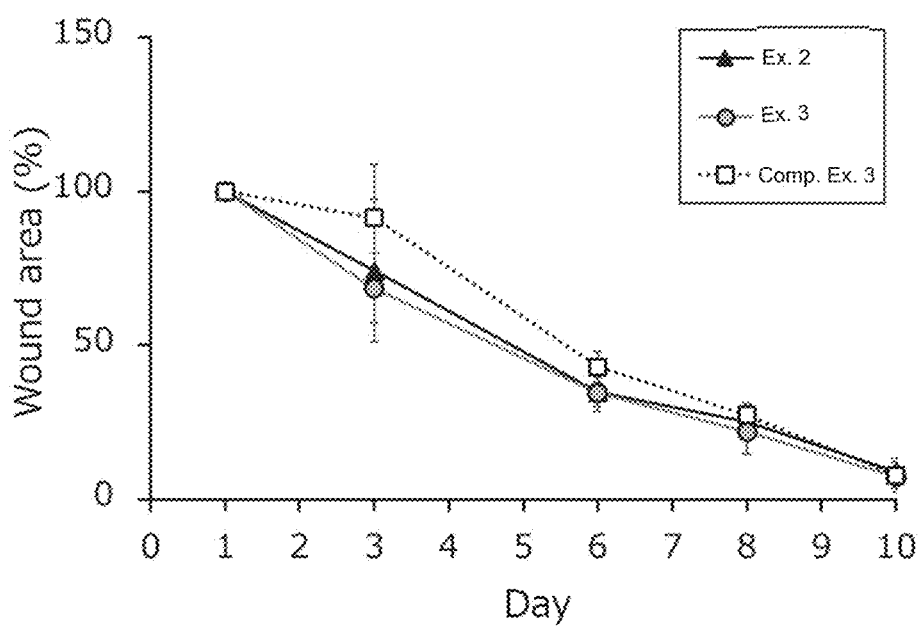
FIG. 13 is a graphical diagram indicative of the results of measurement of skin excision areas in Examples 2 and 3 as well as Comparative Example 3.

Photographs taken of the skin excision are attached hereto as FIG. 12(b), and the results of skin excision area measurement are shown by gray circular markers and a gray solid line in FIG. 13, respectively.

Comparative Example 3

The treatment according to Comparative Example 3 was carried out as in Example 2 except that the constituent used for treating skin wounds was prepared as in Comparative Example 1.

Photographs taken of the skin excision are attached hereto as FIG. 12(c), and the results of skin excision area measurement are shown by white square markers and a dotted line in FIG. 13, respectively.

From comparisons of FIGS. 12(a) and 12(b) with FIG. 12(c), it has been identified that the treatment using the skin wound-treating constituent comprising the sulfide ion-containing LDH introduces some improvement in the skin excision state after the 6 days from the start of treatment. As shown in FIG. 13, it has been identified that in the inventive example using the skin wound-treating constituent comprising the sulfide ion-containing LDH rather than in the comparative example free of it, the skin excision area is smaller from the third day to the sixth day after the start of treatment.

The aforesaid results would imply that the hydrogen sulfide sustained releasing agent-containing constituent for treating skin wounds is applicable not only to bedsores but also to general wounds with healing effects.

Example 4

In Example 4, a skin wound-treating constituent different in structure from the previous one was used to make a study of the efficacy of the invention against a skin excision model.

Figure 14:
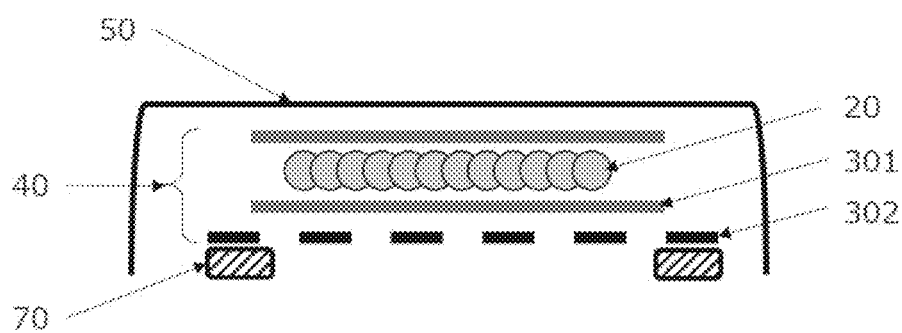
FIG. 14 is a schematic view showing a sectional structure of the constituent for treating skin wounds formed and used in Example 4.

The treatment according to Example 4 was carried out as in Example 2 except that a porous PET plate working as a breathable cover 302 was superposed on one surface of the sustained hydrogen sulfide releaser prepared in Example 1 to form a sustained hydrogen sulfide releaser 40 that was then affixed to a mouse's skin excision via a Plus moist (registered trademark) pad 70 processed in an O-ring shape in such a way as not to come in direct contact with the opening of an excision, and BENELUKE (registered trademark) (made by NIPPON SIGMAX Co., Ltd.) working as a dressing material 50 was affixed onto the releaser 40 to form and apply a skin wound-treating constituent. A sectional structure of the skin wound-treating constituent formed and applied in this example is schematically shown in FIG. 14. In this constituent, the membrane filter and porous PET plate function as breathable covers or sheets 301 and 302, respectively, as shown.

Figures 15A, 15B:
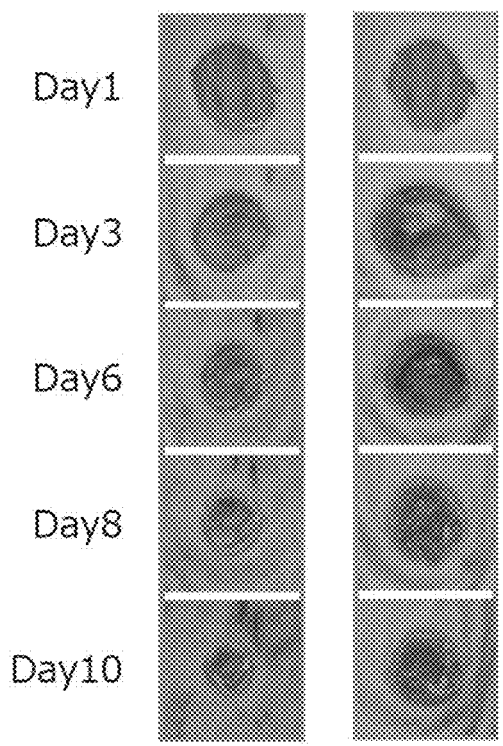
FIGS. 15(a) and 15(b) are sets of photographs showing states of skin excision areas in Example 4 and Comparative Example 4 ((a): Ex. 4, (b): Comp. Ex. 4).
Figure 16:
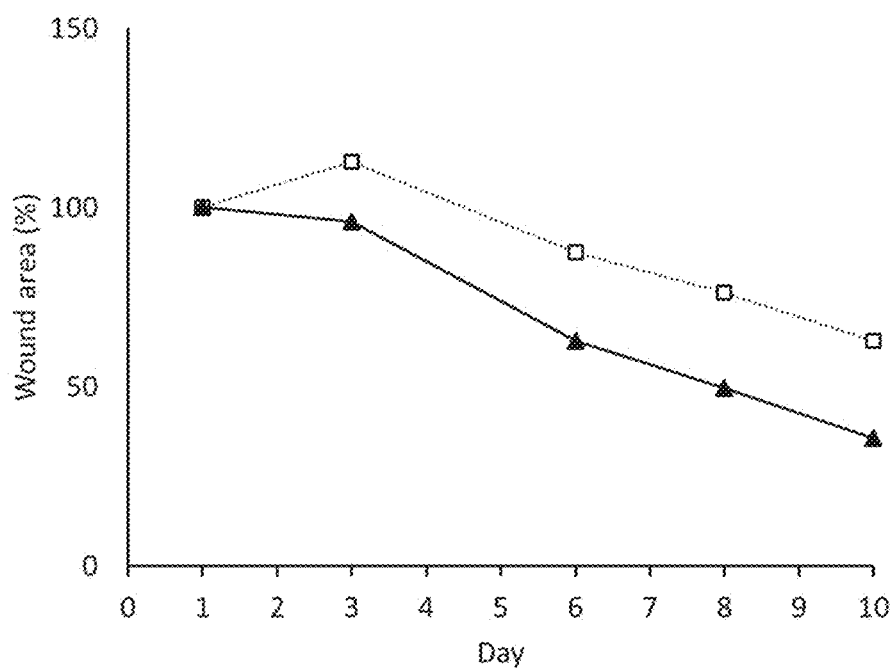
FIG. 16 is a graphical diagram indicative of the results of measurement of skin excision areas in Example 4 and Comparative Example 4.

Photographs taken of the skin excision are attached hereto as FIG. 15(a), and the results of skin excision area measurement are indicated by black triangular markers and a solid line in FIG. 16, respectively.

Comparative Example 4

The treatment according to Comparative Example 4 was carried out as in Example 4 except that no sustained hydrogen sulfide releaser was used in the preparation process of the skin wound-treating constituent.

Photographs taken of the skin excision are attached hereto as FIG. 15(b), and the results of skin excision area measurement are indicated by white square markers and a dotted line in FIG. 16, respectively.

From comparisons of FIG. 15(a) with FIG. 15(b), it has been identified that the treatment using the skin wound-treating constituent comprising the sulfide ion-containing LDH introduces considerable improvements in the skin excision state after the third day from the start of treatment. As can be seen from FIG. 16, it has also been identified that in the inventive example using the skin wound-treating constituent comprising the sulfide ion-containing LDH rather than in the comparative example free of it, the skin excision area reduces noticeably after the third day from the start of treatment. From FIG. 16, it has further been identified that the skin excision area increases until the third day from the start of treatment in the comparative example whereas said area decreases monotonously with each passing day in the inventive example.

The foregoing results would imply that if the skin wound-treating constituent comprising the sustained hydrogen sulfide releasing agent has more optimal structure, it contributes more to healing effects.

Example 5

In Example 5 as well as Comparative Example 5, Example 6 and Comparative Example 6 to be given later, a diabetic mouse was used as the living organism to be treated to make a study of the inventive effect. A diabetic living organism decreases in terms of wound natural healing power; some noticeable wound healing effect would be expected by application of the sustained hydrogen sulfide releasing agent to the skin wound-treating constituent.

The treatment according to Example 6 was carried out as in Example 2 except that a diabetic mouse (C57BL/6J HamSlc-ob/ob mouse at 8-weeks old) was used as the living organism to be treated. Note here that the diabetic mouse used is an obese one as a model of type II diabetes.

Figures 17A, 17B:
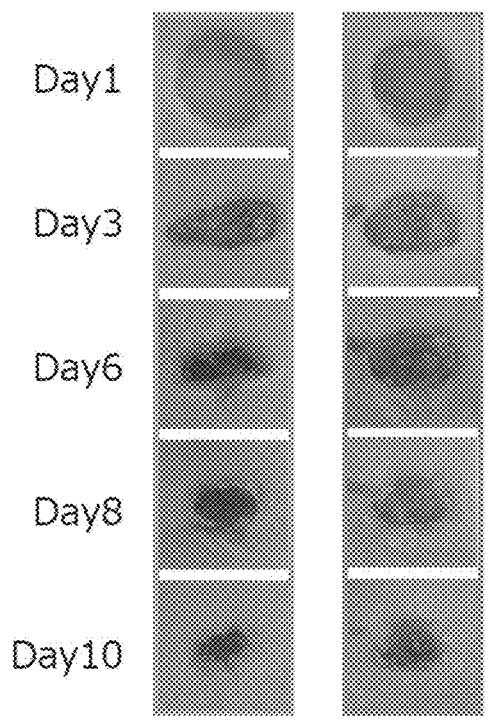
FIGS. 17(a) and 17(b) are sets of photographs showing states of skin excisions in Example 5 and Comparative Example 5 ((a): Ex. 5, (b): Comp. Ex. 5).
Figure 18:
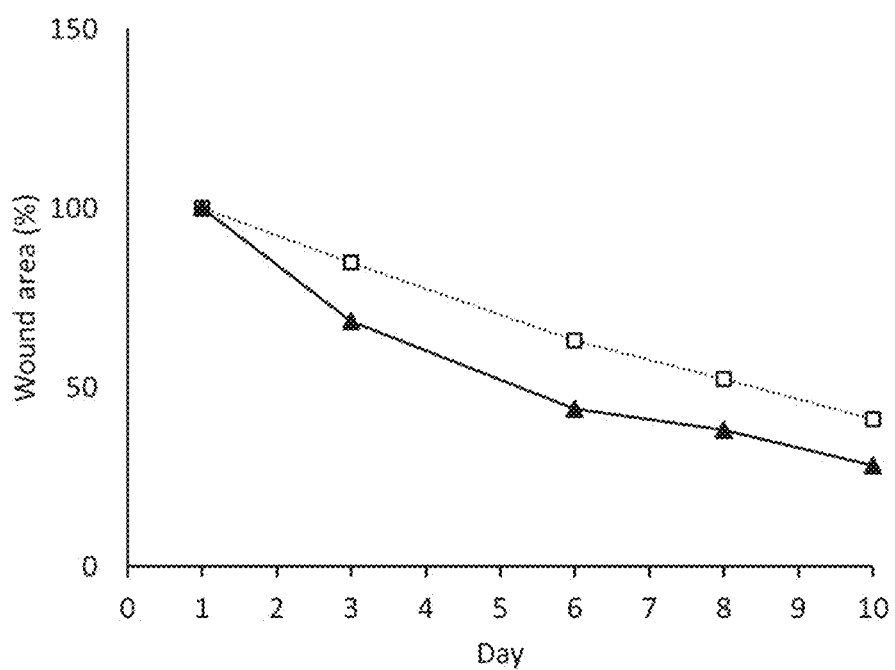
FIG. 18 is a graphical diagram indicative of the results of measurement of skin excision areas in Example 5 and Comparative Example 5.

Photographs taken of the skin excision are attached hereto as FIG. 17(a), and the results of skin excision area measurement are indicated by black triangular markers and a solid line in FIG. 18, respectively.

Comparative Example 5

The treatment according to Comparative Example 5 was carried out as in Comparative Example 3 except that the aforesaid diabetic mouse was used.

Photographs taken of the skin excision are attached hereto as FIG. 17(b), and the results of skin excision area measurement are indicated by white square markers and a dotted line in FIG. 18, respectively.

From comparisons of FIG. 17(a) with FIG. 17(b), it has been identified that the treatment using the skin wound-treating constituent comprising the sulfide ion-containing LDH introduces improvements in the skin excision state after the third day from the start of treatment. As can be seen from FIG. 18, it has been identified that in the inventive example using the skin wound-treating constituent comprising the sulfide ion-containing LDH rather than in the comparative example free of it, the skin excision area decreases after the third day from the start of treatment.

Example 6

The treatment according to Example 6 was carried out as in Example 4 except that the aforesaid diabetic mouse was used as the living organism to be treated, and the cycle comprising application of the skin wound-treating constituent and exposure to the air was repeated 11 times (Day 12).

Figures 19A, 19B:
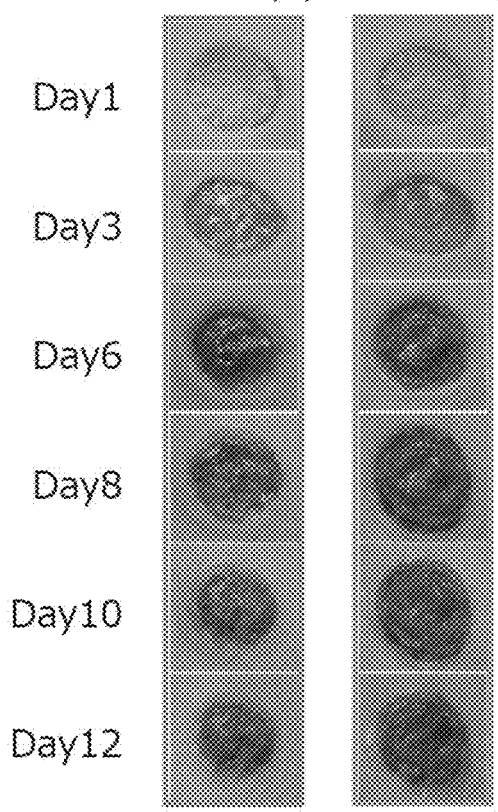
FIGS. 19(a) and 19(b) are sets of photographs showing states of skin excisions in Example 6 and Comparative Example 6 ((a): Ex. 6, (b): Comp. Ex. 6).
Figure 20:
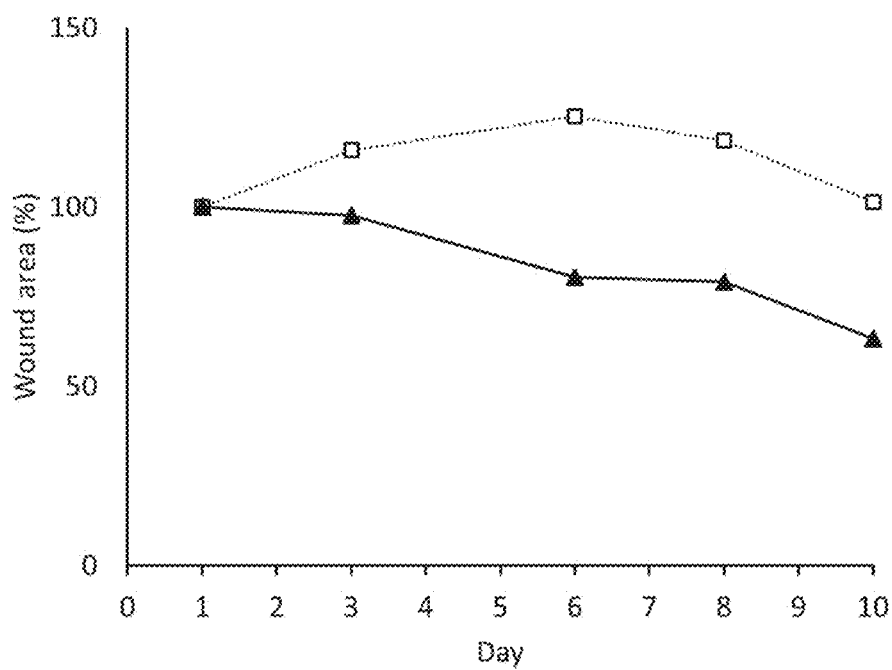
FIG. 20 is a graphical diagram indicative of the results of measurement of skin excision areas in Example 6 and Comparative Example 6.

Photographs taken of the skin excision are attached hereto as FIG. 19(a), and the results of skin excision area measurement are indicated by black triangular markers and a solid line in FIG. 20, respectively. Note here that the area measurement of the skin excision was carried out up to the ninth cycle (Day 10).

Comparative Example 6

The treatment according to Comparative Example 6 was carried out as in Comparative Example 4 except that the aforesaid diabetic mouse was used as the living organism to be treated, and the cycle comprising application of the skin wound-treating constituent and exposure to the air was repeated 11 times (Day 12).

Photographs taken of the skin excision are attached hereto as FIG. 19(b), and the results of skin excision area measurement are indicated by white square markers and a dotted line in FIG. 20, respectively. Note here that the area measurement of the skin excision was carried out up to the ninth cycle (Day 10).

From comparisons of FIG. 19(a) with FIG. 19(b), it has been identified that the treatment using the skin wound-treating constituent comprising the sulfide ion-containing LDH introduces improvements in the skin excision state after the sixth day from the start of treatment. As can be seen from FIG. 20, it has been identified that in the inventive example using the skin wound-treating constituent comprising the sulfide ion-containing LDH rather than in the comparative example free of it, the skin excision area decreases after the third day from the start of treatment. From FIG. 20, it has further been identified that the skin excision area increases until the sixth day from the start of treatment in the comparative example whereas said area decreases monotonously with each passing day in the inventive example.

The foregoing results would reveal that the skin wound-treating constituent comprising the sustained hydrogen sulfide releasing agent is efficacious against living organisms in particular, whose natural healing power remains low due to diseases such as diabetes.

INDUSTRIAL APPLICABILITY

According to the present invention, it is possible to provide a novel method for treating wounds. The present invention is of great value in that it makes the choices of wound-treating methods increase, and in that the treatment complying with the patient's conditions and constitutions as well as demands for treatment methods becomes feasible.

EXPLANATION OF THE REFERENCE NUMERALS

1: Constituent for preventing and/or treating skin wounds
20: Sustained hydrogen sulfide releasing agent
30, 301, 302: Breathable cover or sheet
31: Through-hole
40: Sustained hydrogen sulfide releaser
50: Dressing material
60: Substrate
70: Pad

What is claimed is:
1. A constituent for treating a skin wound comprising:
 a sustained hydrogen sulfide releaser containing a sustained hydrogen sulfide releasing agent, and
 a dressing material on the sustained hydrogen sulfide releaser;
 wherein the sustained hydrogen sulfide releasing agent is a layered double hydroxide having $HS^-$ and/or $S_k^{2-}$ between layers where k is a positive integer.
2. The constituent for treating a skin wound according to claim 1, wherein the layered double hydroxide is represented by a following general formula (1):

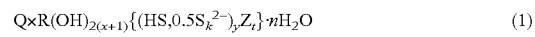

$$Q_x R(OH)_{2(x+1)}\{(HS, 0.5S_k^{2-})_y, Z_t\} \cdot nH_2O \qquad (1)$$

wherein Q is a divalent metal ion, R is a trivalent metal ion, and Z is an anion other than $HS^-$ or $S_k^{2-}$, x is a number that satisfies 1.8≤x≤4.2, y is a number that satisfies 0.01≤y≤2.0, t is a number that satisfies 0≤t≤1.0, and n is a number that changes or varies depending on an environmental humidity.
3. The constituent for treating a skin wound according to claim 1, wherein said sustained hydrogen sulfide releasing agent releases off hydrogen sulfide by contact with the air.
4. The constituent for treating a skin wound according to claim 2, wherein the Q is selected from the group consisting of $Mg^{2+}$, $Mn^{2+}$, $Fe^{2+}$, $Co^{2+}$, $Ni^{2+}$, $Cu^{2+}$, $Zn^{2+}$ and $Ca^{2+}$ and the R is selected from the group consisting of $Al^{3+}$, $Ga^{3+}$, $Cr^{3+}$, $Mn^{3+}$, $Fe^{3+}$, $Co^{3+}$ and $Ni^{3+}$.

5. An ointment for treating a skin wound comprising:
a substrate;
a powdery sustained hydrogen sulfide releasing agent dispersed in the substrate, wherein the powdery sustained hydrogen sulfide releasing agent is a layered double hydroxide having HS$^-$ and/or $S_k^{2-}$ between layers where k is a positive integer.

6. A constituent for treating a skin wound comprising:
a sustained hydrogen sulfide releaser formed by encapsulating a sustained hydrogen sulfide releasing agent within a breathable cover or sheet and
a dressing material on the breathable cover or sheet,
wherein the sustained hydrogen sulfide releasing agent is a layered double hydroxide having HS$^-$ and/or $S_k^{2-}$ between layers where k is a positive integer.

7. The constituent for treating a skin wound according to claim 6, wherein the layered double hydroxide is represented by a following general formula (1):

$$Q \times R(OH)_{2(x+1)}\{(HS, 0.5 S_k^{2-})_y Z_t\} \cdot n H_2O \quad (1)$$

wherein Q is a divalent metal ion, R is a trivalent metal ion, and Z is an anion other than HS or $S_k^{2-}$, x is a number that satisfies $1.8 \leq x \leq 4.2$, y is a number that satisfies $0.01 \leq y \leq 2.0$, t is a number that satisfies $0 \leq t \leq 1.0$, and n is a number that changes or varies depending on an environmental humidity.

* * * * *